US006896909B2

(12) United States Patent
    Fanelli

(10) Patent No.: US 6,896,909 B2
(45) Date of Patent: May 24, 2005

(54) FORMULATIONS CONTAINING IRON ORES FOR THE TOPICAL TREATMENT OF BIOENERGETIC AND ELECTROMAGNETIC DISORDERS

(75) Inventor: Mauro Fanelli, Marta (IT)

(73) Assignee: GeoMedical S.r.l., Marta (IT)

( * ) Notice: Subject to any disclaimer, the term of this patent is extended or adjusted under 35 U.S.C. 154(b) by 37 days.

(21) Appl. No.: 10/139,223

(22) Filed: May 7, 2002

(65) Prior Publication Data

US 2002/0172722 A1 Nov. 21, 2002

(30) Foreign Application Priority Data

May 8, 2001 (IT) ...................................... MI2001A0932

(51) Int. Cl.⁷ ........................ A61K 33/26; A61K 33/00; A61P 17/00; A61P 19/02; A61P 29/00
(52) U.S. Cl. ...................... 424/647; 424/401; 424/489; 424/646; 424/648; 424/724; 514/502; 514/825; 514/886; 514/887; 514/909; 514/951
(58) Field of Search ................................ 424/401, 489, 424/646–648, 724; 514/825, 886, 887, 909, 951, 502

(56) References Cited

U.S. PATENT DOCUMENTS 5,718,908 A * 2/1998 Fanelli .................... 424/401

OTHER PUBLICATIONS

Chemical Abstracts 110:234927 (1989).*
Derwent Abstract, accession No. 1988–108767, abstracting JP 63–57501 (1988).*
Antimony, Guidelines for Canadian Drinking Water Quality: Supporting Documentation, Aug. 1999, pp. 1–9, p. 1 in particular.*

* cited by examiner

*Primary Examiner*—John Pak
(74) *Attorney, Agent, or Firm*—Young & Thompson

(57) ABSTRACT

The invention relates to formulations for the topical treatment of disorders with a bioenergetic basis, which contain a suspension obtainable by treating one or more iron ores with aqueous solutions having pH values of between 4 and 8. These formulations will be applied directly to the acupuncture points corresponding to the meridians involved in the conditions to be treated.

16 Claims, No Drawings

FORMULATIONS CONTAINING IRON ORES FOR THE TOPICAL TREATMENT OF BIOENERGETIC AND ELECTROMAGNETIC DISORDERS

DESCRIPTION OF INVENTION

This invention relates to ore-based formulations for the topical treatment of disorders with a bioenergetic basis.

In particular, the invention relates to topical formulations containing a suspension obtainable by treating iron ores with aqueous solutions having pH values of between 4 and 8.

The formulations of the invention are prepared by suspending suitable iron ores, previously pulverised, in sulphate-alkaline-ferruginous waters or in suitable inorganic salt solutions.

The iron ores used in accordance with the invention include, in particular:
a) Ferrites, especially spinels such as chromite, magnetite and magnesioferrite
b) Ferric oxides and hydroxides such as haematite, limonite and goethite
c) Ferric carbonates such as siderite
d) Sulphides such as pyrrhotine or pyrrhotite, also known as magnetic pyrite or magnetopyrite
e) Disulphides such as pyrite and marcasite
f) Sulphates such as fibroferrite and jarosite
g) Micas such as biotite
h) Chlorites such as chamosite
i) Silicates or metasilicates such as orthorhombic or monoclinic pyroxenes
j) Iron organic compounds.

The compositions of the invention may contain a mixture of iron ores constituted by all the types listed above or only some of them, such as a mixture of ferrites/spinels, carbonates, disulphides, sulphates and chlorites or oxides/hydroxides, sulphides, titanites, micas and silicates. Chlorites, jarosite, marcasite, pyrite and mixtures thereof are particularly preferred.

Metallic iron, for example in the form of iron-bearing sands, iron filings and the like, may be added to the ore suspensions of the invention to further increase their electromagnetic potential.

This potential can be further boosted by subjecting the suspensions, possibly enriched with iron powder, to magnetic fields which impart electromagnetic charges of at least 500 gauss to the suspensions; this is the minimum value for cosmetic applications, while higher values ($\geq 3000$ gauss) are indicated for therapeutic use.

Suspensions of particular ores of volcanic origin are known (EP 0759290) which differ from those forming the object of the invention because they have little or no iron ore content. Known suspensions are based on a totally different application concept associated with antioxidant activity and inhibition of the formation of free radicals of suitably treated volcanic ores.

The novel compositions of this invention have little antioxidant activity, but focus on electromagnetic and bioenergetic properties typical of ores with a high iron content. These properties are to some extent the opposite of the antioxidant and anti-free radical properties of the suspensions described in EP 0759290.

Powdered iron ores, obtained by grinding operations, for example, are suspended in ferruginous sulphate water, possibly after separation by sieving and heat treatment up to 50° C. or magnetic treatment (exposure to pulsating magnetic fields), at the typical rate of 1 kg of ore to 500 ml of water. Suitable rheological agents such as amorphous or microcrystalline silica, diatomaceous earths, and argillaceous phyllosilicates such as montmorillonite, bentonite, smectite, halloysite and the like, can then be added to the suspension.

Iron salts solutions can replace the ferruginous sulphate waters. The pH of the suspensions of the invention is between 4 and 8.

The waters or solutions usable in accordance with the invention will preferably contain other salts, in particular reducing salts, so as to reduce the ferric or ferrous ion content of the ore at least partly to metallic iron, thus further enhancing the magnetic properties of the formulations.

An increase in the metallic iron component can also be obtained at the ore treatment stage, by subjecting iron sulphates, carbonates, oxides or sulphates in particular to suitable degassing of the solutions at high temperature, under vacuum.

The process for preparation of the formulations of the invention comprises the following steps:
1) drying the ore in air current at temperatures of between 20° and 40° C.;
2) grinding without thermal stress;
3) screening to a constant, homogenous particle size of approx. 340 microns;
4) addition of predetermined volumes of aqueous solutions with a suitable pH to the resulting powders.

At step 4), each ore component is added under stirring with turboemulsifiers at high speed for predefined times.

The process is characterised by continuous extraction and recycling of the soluble or finely dispersed phase, the coarser solid components being eliminated by sifting with a vibrating sieve. After dissolving/dispersal, a pre-determined amount of a thickener such as diatomaceous earth is added until the required viscosity is reached.

The formulations of the invention will be presented in the form of ore suspensions packaged in polyethylene-lined aluminium sachets, heat-sealed under a 99.9% vacuum.

The iron ores usable in accordance with this invention may be of synthetic or natural origin, extracted from rocks with a high content of the ore in question, or of volcanic, sedimentary or other origin, provided that they are characterised by the same or very similar chemical and crystallographic compositions and the absence of other inorganic elements liable to interfere adversely with the biological activity of the suspensions of the invention.

These compositions are useful for the cosmetic or therapeutic treatment of a variety of conditions, such as diffuse oedema, local adiposity, vascular lability, excess weight, hypotonicity, dysmetabolism, atonicity, acute and chronic articular and extra-articular muscular degenerative processes with an inflammatory basis, organic hypofunctionality, metabolic disorders, endocrine disorders, hypofunctionality of individual organs and apparatus, inappropriate immune responses, etc.

The main therapeutic indications for the ore suspensions of the invention comprise acute joint disease (arthritis) and chronic joint disease (osteoarthritis), as demonstrated by comparison with classic therapeutic strategies (drugs), instrumental strategies (laser, ultrasound, direct and alternating current) and manual strategies (acupuncture and electroacupuncture).

The therapeutic use of the formulations of the invention is based on the concepts of bioenergetic and electromagnetic remodulation of the affected apparatus and/or organs, thus inhibiting the degenerative processes before they reach them. In fact, measurement of the electromotive force potentials with suitable instruments at the acupuncture and/or electroacupuncture points reveals the hypo/hyperfunctionality of the areas concerned, allowing their bioenergetic remodulation and consequent restoration of the impaired metabolic processes.

The topical formulations of the invention are applied directly to the acupuncture points corresponding to the various meridians involved in the cosmetic or pathological conditions to be treated.

Particular attention should be paid to the application of these ore fractions in the spaces between the fingers and toes, the anatomical areas in which the acupuncture points corresponding to each meridian are most easily found.

The ore suspensions of the invention may be used in association with the ore suspensions with a high antioxidant capacity disclosed in EP 0759290, which perform their specific activity directly in the areas in which they are applied, and can attract the electromagnetic flows released by the iron ore suspensions applied to the peripheral acupuncture points as a result of the potential difference.

Energy is therefore released which flows from the hands or feet towards other areas, modifying their biochemical, functional and reactive characteristics, and synergising the antioxidant and anti-inflammatory action of the antioxidant ore suspensions already known.

The following examples describe the invention in greater detail.

EXAMPLE 1

The types of formulation can be summarised in three different methods.

10 kg of each type of iron ore constituting the 10 groups listed is added separately to 50 l of ferruginous sulphate water or suitably prepared iron salt solution (total 100 kg of ore+50 l of ore solution).

This is followed by centrifugation, sieving and molecular excitation at different temperatures (30/40/50° C.), and a suitable consistency is obtained by adding micronised diatomaceous earths.

The same process can be repeated using only one of the ores listed above or a mixture thereof, such as those constituted by ferrites/spinels, carbonates, disulphides, sulphates and chlorites or oxides/hydroxides, sulphides, micas and silicates.

EXAMPLE 2

STEP A: 30 kg of chlorite-based ore, 10 kg of pyrite, 10 kg of marcasite and 10 kg of jarosite.

STEP B: each ore in the formulation is added successively to a 100 l quantity of sulphate-ferruginous water by centrifugation for 20 minutes at not less than 1200 rpm.

The suspensions are subjected to a first filtration with a vibrating sieve, then 20 kg of bentonite+20 kg of montmorillonite are added. The suspensions are then left to dissolve with a suitable emulsifier overnight (at least 12 hours), refiltered with a vibrating sieve, made up to consistency with 10 kg of diatomaceous earth, homogenised for 24 consecutive hours, and vacuum packed.

This formulation can be used for cosmetic and pharmaceutical purposes, for the treatment of conditions such as such as diffuse oedema, local adiposity, vascular lability, excess weight, hypotonicity, dysmetabolism, atonicity, acute and chronic articular and extra-articular muscular degenerative processes with an inflammatory basis, organic hypofunctionality, metabolic disorders, endocrine disorders, hypofunctionality of individual organs and apparatus, inappropriate immune responses, etc.

What is claimed is:

1. A topical formulation suitable for topical therapeutic or cosmetic applications containing as active principle a suspension obtained by treating with aqueous solution a pulverized iron ore of chlorite, in which the weight ratio between the pulverized ores and the aqueous solution is between 3:1 and 1:3.

2. Formulation as claimed in claim 1, in which the aqueous solution used to prepare the suspension is a natural water.

3. Formulation as claimed in claim 1, in which the pH of a final suspension is between 4 and 8.

4. Formulation as claimed in claim 1, further containing biologically inert excipients and adjuvants.

5. Formulation as claimed in claim 4, in which the inert excipients and adjuvants are amorphous or microcrystalline silica, diatomaceous earth or argillaceous phyllosilicates.

6. Formulation as claimed in claim 5, wherein the argillaceous phyllosilicates are montmorillonite, bentonite, smectite and halloysite.

7. Formulation of claim 2, wherein the natural water is one of sulphate-alkaline-ferruginous water and water with dilutions of inorganic salts.

8. A topical formulation suitable for topical therapeutic or cosmetic applications containing as active principle a suspension obtained by treating with an aqueous solution one or more pulverized iron ores selected from the group consisting of ferrites, spinels, ferric oxide and ferric hydroxide containing iron ores, ferric carbonate iron ores, sulfide containing iron ores, disulfide containing iron ores, sulfate containing iron ores, iron containing micas, iron containing chlorite ores, silicate iron ores, and metasilicate iron ores, said formulation further containing powdered metallic iron derived from iron-bearing sands, iron fillings, or reduction of ferrous/ferric ions by reducing salts present in said aqueous solution.

9. Formulation as claimed in claim 8, in which the iron ore is chromite.

10. Formulation as claimed in claim 8, in which the aqueous solution used to prepare the suspension is one of sulphate-alkaline-ferruginous water, and water with dilutions of inorganic salts.

11. Formulation of claim 10, wherein the aqueous solution used to prepare the suspension is sulphate-alkaline-ferruginous water.

12. Formulation as claimed in claim 8, in which the pH of a final suspension is between 4 and 8.

13. Formulation as claimed in claim 8, in which the weight ratio between the pulverized ores and the aqueous solution is between 3:1 and 1:3.

14. Formulation as claimed in claim 8, further containing biologically inert excipients and adjuvants.

15. Formulation as claimed in claim 14, in which the inert excipients and adjuvants are amorphous or microcrystalline silica, diatomaceous earth or argillaceous phyllosilicates.

16. Formulation as claimed in claim 15, wherein the argillaceous phyllosilicates are montmorillonite, bentonite, smectite and halloysite.

* * * * *